(12) United States Patent
Becherer

(10) Patent No.: US 9,933,633 B1
(45) Date of Patent: Apr. 3, 2018

(54) BIFOCAL CONTACT LENSES PROVIDING REDUCED GLARE AND BLURRINESS IN DIM LIGHTING

(71) Applicant: Paul Douglas Becherer, Belleville, IL (US)

(72) Inventor: Paul Douglas Becherer, Belleville, IL (US)

( * ) Notice: Subject to any disclaimer, the term of this patent is extended or adjusted under 35 U.S.C. 154(b) by 0 days.

(21) Appl. No.: 15/345,786

(22) Filed: Nov. 8, 2016

(51) Int. Cl.
*A61B 3/10* (2006.01)
*A61B 3/02* (2006.01)
*G02C 7/00* (2006.01)
*G02C 7/04* (2006.01)
*G02C 7/10* (2006.01)
*G02C 7/06* (2006.01)
*A61B 3/11* (2006.01)

(52) U.S. Cl.
CPC ............... *G02C 7/044* (2013.01); *A61B 3/02* (2013.01); *A61B 3/112* (2013.01); *G02C 7/063* (2013.01); *G02C 7/104* (2013.01)

(58) Field of Classification Search
USPC ........... 351/200–247, 159.2, 159.14, 159.23, 351/159.02
See application file for complete search history.

(56) References Cited

U.S. PATENT DOCUMENTS

| | | |
|---|---|---|
| 2,415,108 A | 2/1947 | Newman |
| 4,095,878 A | 6/1978 | Fanti |
| 4,573,775 A | 3/1986 | Bayshore |
| 5,071,244 A | 12/1991 | Ross |
| 5,141,301 A | 8/1992 | Morstad |
| 5,245,366 A | 9/1993 | Svochak |
| 5,371,976 A | 12/1994 | Svochak |
| 5,784,145 A * | 7/1998 | Ghodse ................. A61B 3/112 351/205 |
| 5,790,235 A * | 8/1998 | Kirschbaum .......... A61B 3/112 351/206 |
| 6,109,749 A | 8/2000 | Bernstein |
| 6,116,735 A | 9/2000 | Wada |
| 6,120,148 A | 9/2000 | Fiala et al. |
| 6,176,579 B1 | 1/2001 | Mandell |
| 6,199,982 B1 | 3/2001 | Oyama et al. |
| 6,364,483 B1 | 4/2002 | Grossinger et al. |
| 6,685,315 B1 | 2/2004 | De Carle |
| 6,746,118 B2 | 6/2004 | Mandell |
| 6,808,262 B2 | 10/2004 | Chapoy et al. |
| 6,871,953 B1 | 3/2005 | Mandell et al. |
| 6,921,168 B2 | 7/2005 | Lindacher et al. |
| 7,040,757 B2 | 5/2006 | Hall et al. |
| 7,052,133 B2 | 5/2006 | Lindacher et al. |
| 7,503,652 B2 | 3/2009 | Menezes |
| 7,537,338 B2 | 5/2009 | Evans et al. |
| 7,810,925 B2 | 10/2010 | Evans et al. |
| 7,871,162 B2 | 1/2011 | Weeber |

(Continued)

*Primary Examiner* — Mohammed Hasan
(74) *Attorney, Agent, or Firm* — Polster Lieder Woodruff & Lucchesi, L.C.

(57) ABSTRACT

Contact lenses include three or four annular spherical or aspherical optical zones for improved bifocal vision with reduced glare and blurriness in which the boundaries of certain of the distance and near power zones are established in relationship to the user's pupil size at differing illuminations. A device to measure pupil size at varying illuminations to assist in making the improved contact lenses is also disclosed.

14 Claims, 2 Drawing Sheets

(56) References Cited

U.S. PATENT DOCUMENTS

| | | |
|---|---|---|
| 8,231,219 B2 | 7/2012 | Weeber |
| 8,382,281 B2 | 2/2013 | Weeber |
| 8,573,775 B2 | 11/2013 | Weeber |
| 8,672,474 B2 | 3/2014 | Lindacher et al. |
| 8,820,927 B2 | 9/2014 | Weeber |
| 8,858,624 B2 | 10/2014 | Christie et al. |
| 8,894,203 B2 | 11/2014 | Bradley et al. |
| 9,039,172 B2 | 5/2015 | Lindacher et al. |
| 9,304,329 B2 | 4/2016 | Zhao |
| 9,335,563 B2 | 5/2016 | Weeber |
| 9,417,464 B2 | 8/2016 | Wildsmith et al. |
| 9,557,579 B2 | 1/2017 | Lindacher et al. |
| 9,557,580 B2 | 1/2017 | Weeber |
| 2009/0032679 A1* | 2/2009 | Holladay ............... A61F 2/1618 250/201.2 |

\* cited by examiner

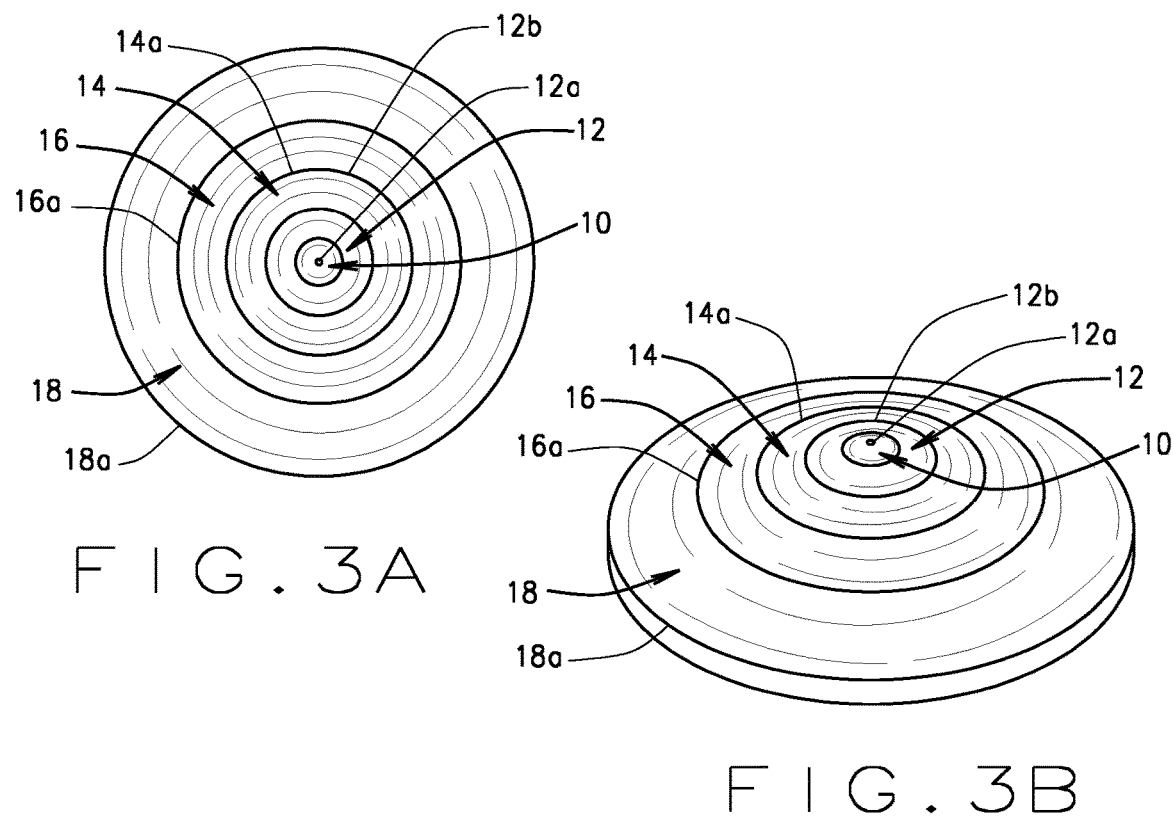
FIG. 3A
FIG. 3B
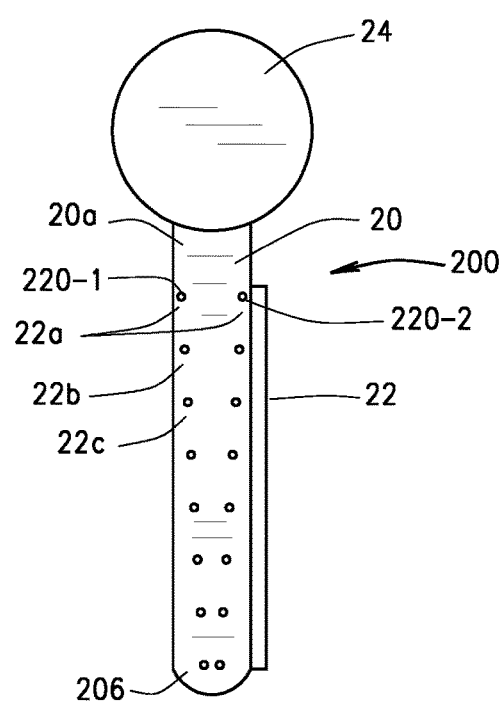
FIG. 4

BIFOCAL CONTACT LENSES PROVIDING REDUCED GLARE AND BLURRINESS IN DIM LIGHTING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The subject matter described herein relates generally to bifocal contact lenses. More specifically, it relates to modified contact lenses to improve vision and reduce glare and blurriness. The invention also involves methods and devices related thereto.

Over one billion people worldwide are estimated to suffer from the eye condition known as presbyopia. Presbyopia, manifested as blurred near vision, results from the normal loss of a person's ability to accommodate or focus using the person's natural crystalline lens. In youth, the brain signals the accommodation muscles of the crystalline lens and the lens adjusts the thickness which alters the focus point of the eye. As a person ages, especially after approximately 40 years of age, the lens changes and slowly loses its ability to focus.

Traditional treatments for presbyopia include the use of bifocal or reading glasses. Another option employed is the use of monovision contacts. With monovision contacts, presbyopes receive contacts in which one eye wears a distance prescription and the other eye wears a prescription for near vision.

For decades, multifocal contact lenses have also been used to aid people that have developed presbyopia. Multifocal contact lenses of this type use two annular zones, multiple zones or aspheric changes to try to aid a person to better see both distant and near objects.

Previous bifocal designs have had powers in the center of the lens to clarify distant objects surrounded by another power that is supposed to be used for reading if the pupil is large enough to utilize the outer zone. In this prior design, the person using this device would see clearly at distance viewing when the pupils are smaller during bright lighting conditions. However, distant objects could become blurred during dim or dark illumination when the pupil becomes larger when responding to the dim illumination. Furthermore, lights at a distance during dim illumination cause halos, resulting in a poorer quality of vision.

Other earlier lens designs have the reading in the center of the lens surrounded by a power to make distant objects clear. In dim illumination when the pupil opens up, the distance may be clear and there may be reduced halos around distant lights; however, during brightly lit conditions when the pupil is small, distant, small objects are not clear.

An issue associated with such contact lenses, however, becomes apparent when the pupil changes aperture size depending on lighting conditions. Thus, the two zone contact lens becomes less ideal when a user's pupil size expands.

In particular, an issue with zonal contact lenses is that under certain conditions, such as at night, when lighting is poor, or during other dimly lit situations, the pupils will enlarge. This results in increased glare and reduced clarity of vision with a standard center distance two zone design for contact lenses.

Accordingly, there is a need for a contact lens which addresses the issue of glare, blurriness and lack of clarity resulting during poorly lit conditions when bifocal contact lenses are used to correct for presbyopia.

BRIEF SUMMARY OF THE INVENTION

As provided below, applicant has addressed the problems of increased glare and blurriness when using bifocal contact lenses at night and under other dimly lit conditions. In particular, a lens design is provided having another distance power surrounding the reading power. In this aspect, when the pupil opens up, this unique design utilizes this extra peripheral distance powered zone thus reducing the halo effect. Additionally, as described herein, in certain aspects of applicant's lens design, it has a distance power in or close to its center. Therefore, when there are small pupils, distant objects appear clear during illuminated conditions.

Thus, a contact lens is provided which addresses the needs and provides the advantages outlined herein. In a first aspect, the contact lens includes three optical zones. A first optical zone includes an optical power for enhancing a user's visual perception of objects at a distance. This first optical zone extends radially outwardly from a central point of the contact lens to a generally annular outer circumference substantially equal to, slightly less than or slightly greater than the user's pupil size during daytime (i.e., bright) illumination. It should be noted that the size of this optical zone will be dependent on the goal of the task of that eye. If the desired task for that eye is to enhance distance vision clarity, the optical zone may be created to approximately equal the size of the pupil or to be slightly larger than the pupil size measured during daytime illumination. If the desired goal for that eye is to enhance the reading or near vision, then the size of the optical zone may be adjusted to be slightly smaller than the pupil during daytime illumination which would result in the reading zone or "zone 2" in this embodiment, being larger. The second optical zone has an optical power for enhancing a user's visual perception of nearby objects or for reading. The second optical zone extends radially from the outer circumference of the first optical zone to an outer circumference slightly smaller than the outer circumference of the user's pupil during dim illumination (applying the principles as explained above). The third optical zone has an optical power for enhancing the user's visual perception of objects at a distance during time intervals of the pupil's increased dilation (applying the principles as explained above). The third zone includes a generally annular, radially extending zone having an inner circumference extending from the outer circumference of the second optical zone to an outer circumference of from about 7 mm to about 9 mm from the central point of the contact lens. The lens design of the right eye is independent from the lens design of the left eye. The lens designs of the right and left eye could match, but if the designer wanted to enhance one eye for distance and the other eye for near, there may be an alteration in the designs between the two lenses to achieve this goal, while still using the three zones approach as described.

Each zone will depend on the person's pupil size during specific lighting conditions and may be altered to enhance workable vision. An example would be if during daylight the person's pupil measured 3.0 mm. and during dark adaptations the pupil measures 6.0 mm. In this example, in one contact lens the center distance zone could be a 2.5 mm central distance zone with a second zone going out to 5.0 mm and the contact lens for the other eye could be a 2.0 mm central distance zone going out to 4.6 mm. In short, the prescriber may alter the zone sizes depending on the needs of the person without departing from the teachings of the invention as described herein.

In another aspect, the contact lens as described above is provided, but includes an aspherical lens. In this aspect, there could be a spherical central distance zone surrounded by an aspheric reading zone in the second zone. For example, the aspheric zone could increase to maximum add in reading power from inside to periphery or could decrease from maximum add to minimal add in periphery.

In another aspect, the contact lens as described above is provided, but it has an aspheric central zone that has the maximum distance power in the center and progressively changes into the reading power radially out from its center. At a chosen amount, for example, 1 mm. less than the maximum dilated pupil as measured in dim illumination, there is a circumscribed ring of distance power. In effect, this combination achieves the same goal of using the outer distance powered ring to reduce or eliminate optical confusion from a physically dilated pupil.

In yet another aspect, the contact lens includes the optical zones as described above, but also includes a small, central reading power zone which is significantly smaller than the user's pupil diameter during bright illumination, which in turn is surrounded by the first distance zone as described above.

The design of the contact lens could be a custom lens based on specific eye and cornea characteristics or could be designed in standard specifications so that a design could be used on a certain group of people having similar eye and cornea characteristics. The lens could be designed so that the lens cosmetically centers the person's cornea or is off-set to align to the person's line-of-sight, the person's angle kappa or the person's angle lambda.

Further, a device for measuring the pupil size of a subject's eyes at more than one illumination is provided. The device is made of a body of material configured to be held in front of the eyes of the subject. Within the material, the device has an array of paired, horizontally spaced holes for peering through the, e.g., opaque material. The paired holes within the array have a range of distances between the holes as measured from the first of the paired holes to the second. Moreover, the array of holes is configured within the body of material so that, at any time the device is being used, the subject can peer through any of the paired, horizontally spaced holes and perceive either one or two holes when the device is held in front of his or her eyes. Further, the array of horizontally spaced holes is configured so that when the device is held in front of the subject's eyes at any predetermined or appropriate illumination, and the subject peers through one or more of the horizontally paired holes, and if a particular set of horizontally paired holes and the space between the holes looks to the subject to approximately be one, rather than two, holes, or two holes side by side depicting a sideways figure eight, the size of his or her pupil during that illumination is determined by that distance.

Methods for obtaining improved bifocal vision using one or more of the improved contact lenses described above are also provided.

Finally, methods for determining the size of a subject's pupil at a given illumination, such as under bright, normal room, or dimly lit illumination, are also provided.

BRIEF DESCRIPTION OF THE DRAWINGS

The presently disclosed subject matter will be better understood from reading the following description of non-limiting embodiments, with reference to the attached drawings, wherein below:

FIGS. 3(a) and (b) are top and perspective views of a contact lens in accordance with a third exemplary embodiment of the present invention depicting a four-zone lens.

FIG. 4 is a front view of a device for measuring the pupil size of a subject at more than one illumination in accordance with an exemplary embodiment of the device.

DETAILED DESCRIPTION OF THE INVENTION

Figure 1A:
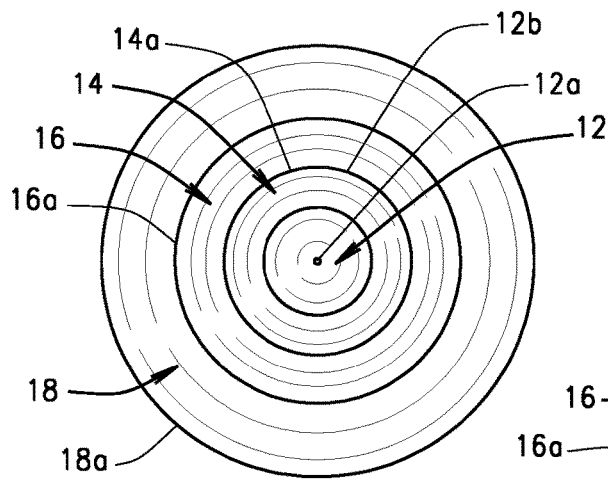
FIGS. 1(a) and (b) are top and perspective views of a contact lens in accordance with a first exemplary embodiment of the present invention depicting a three-zone lens.

The foregoing summary, as well as the following detailed description of certain embodiments will be better understood when read in conjunction with the appended drawings. As used herein, an element or step recited in the singular and preceded with the word "a" or "an" should be understood as not excluding the plural of said elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not including or having that property.

Various embodiments as described and shown herein provide contact lenses which help ameliorate the concern noted above wherein standard bifocal contact lenses produce increased glare and blurring vision when used for naturally mydriatic pupils, e.g., in dimly lit conditions or at night. The contact lenses of the invention address these issues, provide enhanced clarity of vision and other benefits as more fully described herein.

Referring to the drawings, see, e.g., FIGS. 1-4, various embodiments of the contact lens 100 of the invention is provided for a user's eye having a pupil. These lenses, which may be seen to improve both distance and near (or reading) vision for a user suffering from presbyopia, improve clarity of vision and reduce glare and blurriness during dimly lit conditions over standard bifocal contact lenses. In general, the lenses disclosed herein include specific optical zones with distance or near powers, in which some of the sizes of the optical zones, as described herein, are determined by a person's pupil size during different illuminations. Alternatively, these optical zone sizes may be predetermined to set sizes, based on correspondence to known, common pupil sizes during particular illuminations. For example, the lens designs described herein can be mass produced by utilizing the most often designed annular zones to achieve maximum clarity. The base curve and diameter of the lens can be designed, e.g., by using the Arc Length Design or other techniques known to those skilled in the lens-crafting art. In the Arc Length Design technique, in summary, a mathematical formulation based on a person' corneal curvature and the visible iris diameter is employed. Using this design, the lens works well when it rests approximately 2.5 to 3.0 mm outside the limbus of the eye. A lens size based on the average cornea and base curvature amounts of a population (or subgroups within a population), could therefore be utilized.

The lenses of the present invention can be provided without filters, or light filters may be added, e.g., to screen out certain harmful wave lengths. For example, a filter to screen out or reduce penetration of the wave lengths of about 400 to 520 μm would assist in protecting the eye from damage while reading using certain types of devices that emit in those wave lengths. A portion of the lens, all, or substantially all of the lens could be tinted or have this protection.

Accordingly, in the embodiment shown in FIGS. 1 (a) and (b), the contact lens 100 includes a first (and in this embodiment, typically central) optical zone 12 having a power that relates to the user's normal distance prescription. This first optical zone extends radially outwardly from a central point 12a of the contact lens to a generally annular outer circumference 12b substantially equal to, slightly less than or slightly greater than the user's pupil size during bright illumination. The contact lens 100 has a second optical zone 14 which has an optical power for enhancing a user's visual perception of nearby objects or for reading. The second optical zone 14 extends radially from the outer circumference of the first optical zone 12b to an outer circumference 14a slightly smaller than the outer circumference of the user's pupil during dim illumination. In this embodiment, the lens has a third optical zone 16 which has an optical power for enhancing the user's visual perception of objects at a distance during time intervals of the pupil's increased dilation. The third zone 16 comprises a generally annular, radially extending zone having an inner circumference 14a extending from the outer circumference of the second optical zone 14a to an outer circumference 16a to about 8 mm or more, i.e., a distance sufficient to provide the desired effect of enhancing the particular user's distance perception during time intervals of increased dilation. Such ranges may include, e.g., of from about 7 mm to about 9 mm, from about 7¼ mm to about 8¾ mm, from about 7½ mm to about 8½ mm, from about 7¾ mm to about 8¼ mm, and about 8 mm, measured from a central point 12a of the contact lens 100.

In the typical contact lens, the final optical zone (here the third) is surrounded by a zone which serves as a fitting part 18 to assist in better fitting the lens 100 to the eye of the lens' user. The fitting part 18 includes a generally annular, radially extending zone having an inner circumference extending from the outer circumference 16a of the third optical zone 16 to the outer circumference 18a of the lens itself. Typically, the outer circumference of the fitting part (and the lens itself) 18a may be anywhere from about 10.0 mm to about 17.00 mm, more or less, depending on the size and particular shape of the eyes for which the lens 100 is being fitted.

Figure 1B:
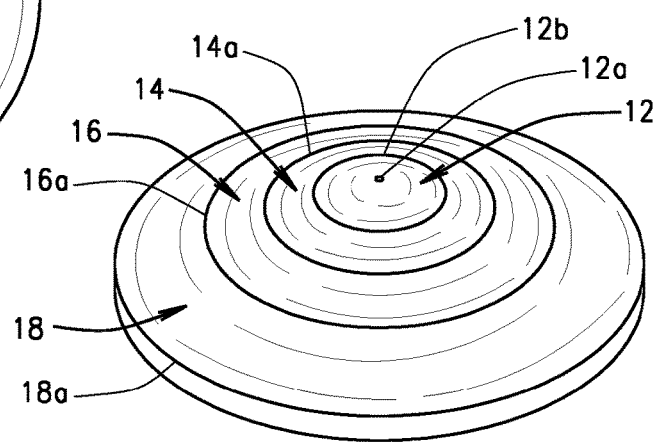
Figure 2A:
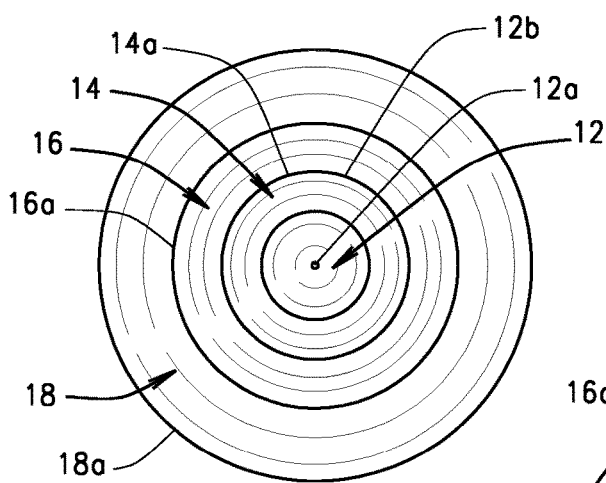
FIGS. 2(a) and (b) are top and perspective views of a contact lens in accordance with a second exemplary embodiment of the present invention depicting a three-zone, aspherical lens.
Figure 2B:
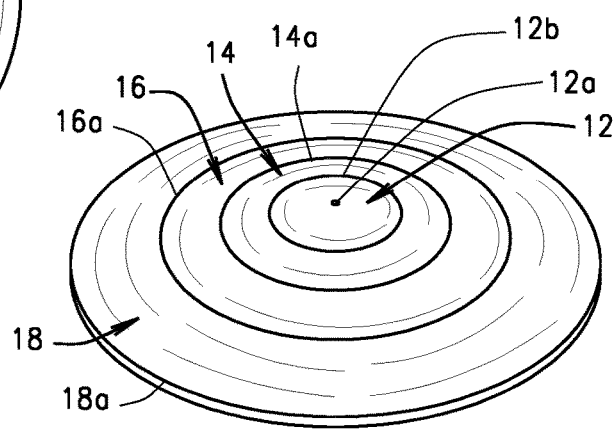

In another embodiment, shown at FIGS. 2 (a) and (b), the contact lens 100 contains all of the zones and features of the embodiment of the contact lens shown in FIGS. 1(a) and 1(b). However, as shown at 22 (see FIGS. 2 (a) and (b)) in this embodiment, the lens is aspherical. This change in the lens from spherical to aspherical provides for a gradual change in the power of the lens using asphericity rather than a set power using a spherical design, while also providing the benefits of increased clarity of vision, reduced glare and reduced blurriness during time intervals of increased pupil dilation by having the third zone having distance power.

In yet another embodiment, shown at FIGS. 3 (a) and (b), a contact lens 100 is provided for a user's eye having a pupil comprising four optical zones. In this embodiment, a very small reading power zone 10 is added centrally that is significantly smaller than the user's pupil diameter during bright illumination. In this embodiment, the first (and in this embodiment, the central) optical zone 10 comprises an optical power for enhancing a user's visual perception of nearby objects or for reading. The first optical zone 10 extends radially outwardly from a central point 12a on the lens to about 1 mm, again, more or less, depending on the size and particular shape of the eyes for which the lens 100 is being fitted. In an embodiment illustrated herein, this comprises the outer circumference 10a of the first optical zone 10 and also the inner circumference 10a of the second (distance power) optical zone 12, described below.

In this embodiment, the second optical zone 12 comprises an optical power for enhancing a user's visual perception of objects at a distance. The second optical zone 12 comprises a generally annular, radially extending zone having an inner circumference 10a extending from the outer circumference 10a of the first optical zone 10, described above, and extending to a generally annular outer circumference 12b substantially equal to, slightly less than or slightly greater than the user's pupil size during bright illumination.

In this embodiment, the lens has a third optical zone 14 having an optical power for enhancing a user's visual perception of nearby objects or for reading. This third optical zone 14 comprises a generally annular, radially extending optical zone having an inner circumference 12b extending from the outer circumference 12b of the second optical zone 12 to an outer circumference 14a slightly smaller than the outer circumference of the user's pupil during dim illumination.

In this embodiment, the lens has a fourth optical zone 16 having an optical power for enhancing the user's visual perception of objects at a distance during time intervals of the pupil's increased dilation. The fourth optical zone 16 comprises a generally annular, radially extending zone having an inner circumference 14a extending from the outer circumference 14a of the third optical zone 14 to an outer circumference 16a, again, dimensioned as described above for the outmost zone in that embodiment.

The results of these zonal embodiments, as described herein, may also be accomplished by using the same arrangement of powers, but by using aspheric, progressive or degressive powers Thus, the reading zone, whether it is the $2^{nd}$ zone in the 3 power grid lens or the reading zone in the $3^{rd}$ zone in the 4 power grid design having a small reading zone in the center, may be either spherical or aspheric. If spherical, it would have a single magnification power consistently in that ring. However, in an aspheric version, the magnification power can change from minimum magnification to a maximum magnification as chosen by the prescriber. This power can increase in magnification from the more central portion to the periphery or can decrease from the maximum magnification to the minimum magnification.

Another alternative embodiment is designed to alter either or both of the distance power zones to be either stronger or weaker than the person's prescription. The prescriber may find that a person is more comfortable being under-corrected in either the central distance power (12) or the peripheral distance power (16), or may find visual or comfort benefit from either (12) or (16) from being altered to a different power.

As described previously, in the typical contact lens, the final optical zone is surrounded by a zone which serves as a fitting part 18 to assist in better fitting the lens 100 to the eye of the lens' user. As depicted in FIGS. 3 (a) and (b), the fitting part 18 includes a generally annular, radially extending zone having an inner circumference 16a extending from the outer circumference 16a of the fourth optical zone 16 to the outer circumference of the lens itself 18a. Typically, the outer circumference of the fitting part (and the lens itself) may be anywhere from about 10 mm to about 17.0 mm, more or less, depending on the size and particular shape of the lens user's eyes.

The above lenses described herein may include a spherical, a spherical and cylindrical, or as depicted in FIGS. 2 (a) and (b), an aspherical correction. The lenses can be custom created or mass produced to set specifications. In determining a "central point" for the alignment of the central zone, the determination can be based on a geometric center on the person's cornea, or can be offset to align to the person's angle lambda, angle kappa, or line of sight.

As known to one skilled in this art, the lenses can be constructed with a variety of materials, including soft (e.g., hydrogel, hema, glycerol and silicone hydrogel), rigid (e.g., polymethylmethacryllate, and silicon-acrylate) or a hybrid material combining any of the soft and rigid materials mentioned and including any new materials developed.

Additionally, the astigmatic power can be stabilized by various methods, including a prism ballasted method, a double slab off method, a combination of prism ballasted and slab-off, or by controlling the thickness utilizing gravity or eyelid pressure to maintain the proper power positioning.

To assist in construction of the lenses of the invention, a person's pupils should be critically measured. Standard pupil measuring devices are often overly expensive (e.g., requiring electronic, computerized and/or photographic instrumentation) and are limited in measuring the pupil to only when certain illumination or lighting conditions are present.

A device 200 for measuring pupil size of a subject's eyes at more than one illumination is shown in FIG. 4. The device 200 comprises a body of material 20 configured to be held in front of the eyes of the subject. As shown in FIG. 4, in a particular embodiment, the body has a first end 20a and a second end 20b.

Within the body of material 20, the device 200 has an array 22 of paired, horizontally spaced holes 22a, 22b, 22c, etc. for peering through the body of material 20 comprising a range of distances between the holes as measured from a first one 22a-1 of the paired holes to a second one 22a-2 of the paired holes within the array 22, the array 22 being configured within the body of material 20 so that the subject can peer through any of the paired, horizontally spaced holes (e.g., 22a) and visually perceive either one or two holes when the device 200 is held in front of the subject's eyes. In an embodiment, the device 200 has 36 or less paired holes, and covers from about 2 mm to 10 mm. In a preferred embodiment, the device 200 has 36 holes, arranged as 18 sets of holes (22a, etc.) spaced in ½ mm increments from 2 mm to 10 mm. One skilled in the art would know to alter hole numbers and spacing, e.g., to achieve economies or to add additional functionalities into the device.

The array 22 of horizontally spaced holes is configured so that when the device is held in front of the subject's eyes at any particular illumination, and the subject peers through one or more of the horizontally paired holes (22a, etc.), when a particular set of horizontally paired holes and the space between the holes appears to the subject to be one, rather than two holes, the size of the pupil during that illumination is determined.

For example, as depicted in the embodiment shown at FIG. 4, the device 200 can be a flat, thin, opaque piece of plastic or other body of material 20 capable of being placed or held in front of a subject's pupil. As shown in this embodiment, the set or array 22 of paired horizontally spaced holes 22a, 22b, etc., start out at about, e.g., 10 mm, more or less, and the user peers through the device at that point. If the person is able to detect two separate holes going back and forth between the pair of holes, e.g., 22c, at the selected distance between them, then the two holes' distance is larger than the person's pupil. However, as the person moves down the array 22 of horizontally spaced paired holes, in this embodiment, the distance shrinks with each set being closer together. At some point, the two holes and the space between the two holes is less than the size of the pupil at the illumination in question, and will seem like one, rather than two, holes. This occurs when both holes and the area between the holes is located within the pupil size. Thus, this indicates the approximate size of the pupil during that specific illumination.

Preferably, the device is configured to measure the pupil during three different stages of illumination—bright (i.e., approximately 1,000 foot candles (ftcd)), average room lighting (i.e., approximately 60 ftcd) and dim illuminations (i.e., approximately 1 ftcd). The measurements can then be employed to determine the inner and outer circumferences of certain of the various optical zones as described above.

In a preferred embodiment, the measuring device is designed to include an occluder 24 or other attachment/portion which can provide additional information during the examination. The additions are for convenience so the device could be used to provide other services. The device could have an occluder so it could be used to cover an eye and block reading material or letters for the blocked eye. The device could have a metric or inch ruler or both on it. It could have conversion charts printed on it, for example diopter to millimeter conversion for radius of curvature. It could have a conversion chart for vertex distance for dioptric powers from the spectacle plane to the corneal plane. The available space on the device could have information printed on with information to aid in the examination of that person or it could have advertising information printed on it.

In its various embodiments, the contact lens of the invention are designed to be utilized via placement on the user's eye to significantly reduce or eliminate glare and blurriness in dim lighting conditions. As used, the contact lens compensates for the person's ametropia resulting in clearer vision at distance while another portion of the contact lens compensates for the loss of accommodation or ability to clear near objects due to age.

Thus this invention in its various embodiments serves to significantly reduce or eliminate the problem of glare and blurriness for bifocal contact lens.

It is to be understood that the above description is intended to be illustrative, and not restrictive. For example, the above-described embodiments and/or aspects thereof may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the following claims, the terms "first," or "second," etc. are used merely as labels, and are not intended to impose numerical requirements on their objects.

This written description uses drawings and examples of components to disclose various embodiments of the invention, including the best mode, and also to enable any person skilled in the art to practice the various embodiments of the invention, including making and using any devices or systems and performing incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A contact lens for a user's eye having a pupil comprising:
   a first optical zone comprising an optical power for enhancing a user's visual perception of objects at a distance wherein the first optical zone extends radially outwardly from a central point on the contact lens to a generally annular outer circumference substantially equal to, slightly less than or slightly greater than the user's pupil size during bright illumination;
   a second optical zone having an optical power for enhancing a user's visual perception of nearby objects or for reading wherein the second optical zone extends radially from the outer circumference of the first optical zone to an outer circumference slightly smaller than the outer circumference of the user's pupil during dim illumination; and,
   a third optical zone having an optical power for enhancing the user's visual perception of objects at a distance during time intervals of the pupil's increased dilation, comprising a generally annular, radially extending optical zone having an inner circumference extending from the outer circumference of the second optical zone to an outer circumference of from about 7 mm to about 9 mm from the central point of the contact lens.

2. A contact lens as set forth in claim 1 wherein the outer circumference of the third optical zone is about 8 mm from the central point on the contact lens.

3. The contact lens of claim 1 wherein all, substantially all, or at least a portion of the lens comprises a light filter to screen out or inhibit penetration to the user's eye of predetermined wavelengths of light.

4. The contact lens of claim 3 wherein the light filter is configured to screen out or inhibit wavelengths of from about 400 to about 520 $\mu$m to protect the user's eye.

5. An aspherical contact lens for a user's eye having a pupil comprising:
   a first optical zone comprising an optical power for enhancing a user's visual perception of objects at a distance wherein the first optical zone extends radially outwardly from a central point on the contact lens to a generally annular outer circumference substantially equal to, slightly less than, or slightly greater than the user's pupil size during bright illumination;
   a second optical zone having an optical power for enhancing a user's visual perception of nearby objects or for reading wherein the second optical zone extends radially from the outer circumference of the first optical zone to an outer circumference slightly smaller than the outer circumference of the user's pupil during dim illumination; and,
   a third optical zone also having an optical power for enhancing the user's visual perception of objects at a distance during time intervals of the pupil's increased dilation, comprising a generally annular, radially extending optical zone having an inner circumference extending from the outer circumference of the second optical zone to an outer circumference of from about 7 mm to about 9 mm from the central point of the contact lens.

6. A contact lens as set forth in claim 5 wherein the outer circumference of the third zone optical zone is about 8 mm from the central point on the contact lens.

7. The contact lens of claim 5 wherein all, substantially all, or at least a portion of the lens comprises a light filter to screen out or inhibit penetration to the user's eye of predetermined wavelengths of light.

8. The contact lens of claim 7 wherein the light filter is configured to screen out or inhibit wavelengths of from about 400 to about 520 $\mu$m to protect the user's eye.

9. A contact lens for a user's eye having a pupil comprising:
   a first optical zone comprising an optical power for enhancing a user's visual perception of nearby objects or for reading wherein the first optical zone extends radially outwardly from a central point on the contact lens to about 1 mm;
   a second optical zone comprising an optical power for enhancing a user's visual perception of objects at a distance wherein the second optical zone comprises a generally annular, radially extending optical zone having an inner circumference extending from the outer circumference of the first optical zone and extending to a generally annular outer circumference substantially equal to, slightly less than or slightly greater than the user's pupil size during bright illumination;
   a third optical zone having an optical power for enhancing a user's visual perception of nearby objects or for reading comprising a generally annular, radially extending optical zone having an inner circumference extending from the outer circumference of the second optical zone to an outer circumference slightly smaller than the outer circumference of the user's pupil during dim illumination; and
   a fourth optical zone having an optical power for enhancing the user's visual perception of objects at a distance during time intervals of the pupil's increased dilation, comprising a generally annular, radially extending optical zone having an inner circumference extending from the outer circumference of the third optical zone to an outer circumference of from about 7 mm to about 9 mm from the central point of the contact lens.

10. A contact lens as set forth in claim 9 wherein the outer circumference of the fourth optical zone is about 8 mm from the central point on the contact lens.

11. The contact lens of claim 9 wherein all, substantially all, or a portion of the lens comprises a light filter to screen out or inhibit penetration to the user's eye of predetermined wavelengths of light.

12. The contact lens of claim 11 wherein the light filter is configured to screen out wavelengths of from about 400 to about 520 $\mu$m to protect the user's eye.

13. The contact lens of claim 9 wherein one or more of the optical powers comprise aspheric progressive or degressive powers.

14. The contact lens of claim 9 wherein one or more of the optical powers providing for enhancing the user's visual perception of objects at a distance is stronger or weaker than the user's normal distance optical prescription.

\* \* \* \* \*